US008921065B2

(12) United States Patent
Chu et al.

(10) Patent No.: US 8,921,065 B2
(45) Date of Patent: Dec. 30, 2014

(54) REAGENT COMPOSITION FOR ELECTROCHEMICAL BIOSENSORS

(75) Inventors: Amy H. Chu, Elkhart, IN (US); Hope G. Spradlin, Granger, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 1218 days.

(21) Appl. No.: 11/885,237

(22) PCT Filed: Mar. 3, 2006

(86) PCT No.: PCT/US2006/007875
§ 371 (c)(1),
(2), (4) Date: Aug. 28, 2007

(87) PCT Pub. No.: WO2006/096619
PCT Pub. Date: Sep. 14, 2006

(65) Prior Publication Data
US 2008/0199937 A1      Aug. 21, 2008

Related U.S. Application Data

(60) Provisional application No. 60/658,634, filed on Mar. 4, 2005.

(51) Int. Cl.
*C12Q 1/32* (2006.01)
*C12N 9/24* (2006.01)
*C12M 1/34* (2006.01)
*C12Q 1/00* (2006.01)

(52) U.S. Cl.
CPC .............. *C12Q 1/004* (2013.01); *C12Q 1/006* (2013.01)
USPC ........................... 435/26; 435/200; 435/287.1

(58) Field of Classification Search
USPC ........................................ 435/26, 200, 287.1
See application file for complete search history.

(56) References Cited

U.S. PATENT DOCUMENTS

| | | | |
|---|---|---|---|
| 5,120,420 A | 6/1992 | Nankai et al. ............... 204/403 |
| 5,320,732 A | 6/1994 | Nankai et al. ............... 204/403 |
| 5,429,735 A | 7/1995 | Johnson et al. .............. 204/403 |
| 5,660,791 A | 8/1997 | Brenneman et al. ........... 422/58 |
| 5,682,884 A | 11/1997 | Hill et al. ..................... 128/637 |
| 5,708,247 A | 1/1998 | McAleer et al. ............. 204/403 |
| 5,798,031 A | 8/1998 | Charlton et al. ............. 204/403 |
| 5,951,836 A | 9/1999 | McAleer et al. ............. 204/403 |
| 5,958,199 A | 9/1999 | Miyamoto et al. ........... 204/403 |
| 5,997,817 A * | 12/1999 | Crismore et al. .......... 204/403.1 |
| 6,059,946 A | 5/2000 | Yukawa et al. |
| 6,241,862 B1 | 6/2001 | McAleer et al. ............. 204/403 |
| 6,270,637 B1 | 8/2001 | Crismore et al. ............ 204/403 |
| 6,455,001 B1 | 9/2002 | Knappe et al. ................. 422/56 |
| 6,531,040 B2 | 3/2003 | Musho et al. ................ 204/401 |
| 6,656,702 B1 | 12/2003 | Yugawa et al. ................ 435/26 |
| 6,736,957 B1 | 5/2004 | Forrow et al. .............. 205/777.5 |
| 6,773,564 B1* | 8/2004 | Yugawa et al. .......... 204/403.14 |
| 2003/0205464 A1 | 11/2003 | Taniike et al. ........... 204/403.14 |
| 2004/0157339 A1 | 8/2004 | Burke et al. ................. 436/149 |
| 2005/0008537 A1* | 1/2005 | Mosoiu et al. ................. 422/56 |
| 2005/0139489 A1* | 6/2005 | Davies et al. ................ 205/775 |

FOREIGN PATENT DOCUMENTS

| | | |
|---|---|---|
| EP | 0 992 589 A2 | 4/2000 |
| JP | 09140378 A  * | 6/1997 |
| WO | 2004/113917 A2 | 12/2004 |
| WO | WO 2004/113917 A2 | 12/2004 |

OTHER PUBLICATIONS

Written Opinion of the International Searching Authority corresponding to co-pending International Patent Application No. PCT/US2006/007875, European Patent Office, dated Aug. 29, 2006, 9 pages.
International Search Report corresponding to co-pending International Patent Application No. PCT/US2006/007875, European Patent Office, dated Aug. 29, 2006, 5 pages.
Laurinavicius V et al., "Oxygen Insensitive Glucose Biosensor Based on PQQ-Dependent Glucose Dehydrogenase," Analytical Letters, vol. 32, No. 2, Jan. 1999.

* cited by examiner

*Primary Examiner* — Susan Hanley
*Assistant Examiner* — Paul Martin
(74) *Attorney, Agent, or Firm* — Nixon Peabody LLP

(57) ABSTRACT

A reagent composition containing GDH-PQQ as an enzyme-co-factor and screen-printed on working and counter electrodes of electrochemical biosensors, maintains activity of the enzyme reagents by proper selection of components. A preferred composition includes hydrophilic polymers, amorphous untreated silica, buffers, surfactants, and a mediator. For example, the biosensor is useful in the amperometric determination of glucose.

28 Claims, 6 Drawing Sheets

REAGENT COMPOSITION FOR ELECTROCHEMICAL BIOSENSORS

CROSS-REFERENCE TO RELATED APPLICATIONS

This application claims priority to Application No. 60/658,634 filed on Mar. 4, 2005, which is incorporated by reference in its entirety.

This application claims priority under 35 U.S.C. §371 to PCT Application No. PCT/US06/07875, filed Mar. 3, 2006.

FIELD OF THE INVENTION

This invention is directed generally to the field of medical devices that are used to analyze biological fluids.

BACKGROUND OF THE INVENTION

More specifically, this invention relates to the biosensors that are used to measure the amount of analytes in bodily fluids, particularly in measuring glucose in samples of whole blood. Optical methods are often used for making such measurements, but the present invention relates to improvements in electrochemical biosensors.

Although the methods of the invention to be described herein can be applied to measuring other analytes, measuring glucose in whole blood samples is of particular interest. The invention also relates to an electrochemical instrument in which a constant or varying potential is applied to electrodes in contact with a blood sample and the resulting current is measured after a short period of time. The measured electrical current is correlated with the amount of the analyte in the sample. Such instruments are referred to as amperometric.

Glucose biosensors used in amperometric instruments may employ a number of reagent systems that react enzymes with the glucose in the sample and produce a measurable electrical current by oxidation of a redox compound, referred to as a mediator in the following general sequence of steps:

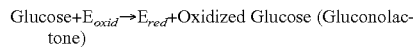
Glucose+$E_{oxid}$→$E_{red}$+Oxidized Glucose (Gluconolactone)

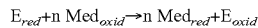
$E_{red}$+n $Med_{oxid}$→n $Med_{red}$+$E_{oxid}$

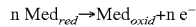
n $Med_{red}$→$Med_{oxid}$+n $e^-$

Where $E_{oxid}$ and $E_{red}$ are oxidized and reduced forms of the redox center of the enzyme and $Med_{oxid}$ and $Med_{red}$ are the oxidized and reduced forms of the mediator. Glucose oxidase has been used as the enzyme in electrochemical biosensors, but more recently, glucose dehydrogenase has been introduced. These enzymes are used with a co-enzyme or co-factor, such as NAD, FAD, and PQQ. The mediator may be ferricyanide or a tetrazolium salt, among others familiar to those skilled in the art.

Glucose dehydrogenase (GDH), its co-factor, and the mediator are combined in a formulation that is applied to a pair of electrodes, described as the working and counter electrodes. When a potential is applied across the electrodes, the enzyme/co-factor oxidizes the glucose (the analyte) and the mediator is reduced as it reoxidizes the enzyme. The reduced mediator migrates to the working electrode where it is reoxidized, and in the process releases electrons that move to the counter electrode and establish an electrical current that is proportional to the amount of the glucose present in the sample.

Since a new sensor is used each time a patient tests the amount of glucose in their blood, reagent formulations should provide consistent performance from one biosensor to the next. Clearly, it is important that the results are reliable, because the users will adjust their diet or medication in response to the results of their tests. Therefore, among other requirements, the enzyme should maintain its activity throughout its useful shelf life. The present invention relates in particular to limiting or preventing the loss of activity of an enzyme/co-factor system [i.e., glucose dehydrogenase-pyrrolo-quinoline quinone (GDH-PQQ)] used in electrochemical biosensors.

One method of maintaining activity of GDH-PQQ is suggested in U.S. Pat. No. 6,656,702, which teaches the addition of sugars to the reagent formulations, particularly trehalose with GDH-PQQ. In one example a hydrophilic polymer, carboxymethyl cellulose, is deposited on the electrodes and dried. Then, the reagent mixture, including GDH-PQQ, trehalose, and potassium ferricyanide as the electron acceptor (mediator), was deposited by "dropping" on the dried carboxymethyl cellulose layer and then dried to complete the reagent layer on the electrodes. The patent also suggests that a hydrophilic polymer could also be added to the layer that contains the reagents. It is believed that the '702 patent by referring to "dropping" of the reagent layers means that they were deposited by dispensing reagent droplets into a well surrounding the exposed electrodes.

Another patent (U.S. Pat. No. 6,270,637) describes a formulation for electrochemical biosensors that includes GDH-PQQ and also includes hydroxyethyl cellulose. The patent stresses the value of including polyethylene oxide having a molecular weight of 100 to 900 kilodaltons (kDa). The method of applying their formulation on the electrodes is not provided in detail, but it is believed to be done by dispensing reagent with a pump system.

Screen printing of reagent layers was used in the compositions and biosensors described in U.S. Pat. Nos. 5,708,247; 5,951,836; and 6,241,862. Glucose oxidase was used as the enzyme and the reagent compositions also included hydroxyethyl cellulose and a treated silica that was selected to have a balance of hydrophobicity and hydrophilicity, said to form two-dimensional networks that exclude red blood cells.

Reagent formulations may be deposited by various methods, including impregnation, stripe coating, ink-jet printing, or micro-deposition with a syringe pump that may include the addition of a micro-solenoid valve drop ejection device. Screen printing is a method of particular interest since it is efficient and well adapted to large scale production of biosensors. It requires that the formulation (i.e., the ink) applied to the electrodes has certain physical properties to be successfully applied. In particular, the inks applied by screen-printing should have the following properties: adhesion to the substrate, cohesion, thixotropy (shear thinning), and optimized rheology for viscosity and flow.

The present inventors found that a composition, which was used for screen printing when glucose oxidase was the enzyme, could not be used when the enzyme was changed to GDH-PQQ, because the new enzyme lost activity rapidly. After investigation, it was determined that certain of the components used to provide the necessary physical properties for screen printing caused the loss of enzyme activity. Consequently, it was necessary to discover components that would not cause premature deactivation of the GDH-PQQ, but also meet the requirements for screen printing. Those reagent formulations are described below.

SUMMARY OF THE INVENTION

The invention in one aspect is a reagent composition for application to the electrodes in electrochemical biosensors.

The new composition can be screen printed and avoids premature loss of activity of the enzyme-co-factor system (GDH-PQQ) used to oxidize glucose in a glucose biosensor. In a preferred embodiment, the GDH-PQQ is combined with a hydrophilic polymer, preferably hydroxyethyl cellulose, and amorphous hydrophilic silica powder in a buffer solution maintaining a pH between 4.5 and 6.5, a surfactant, and a mediator, preferably ferricyanide.

In one embodiment, the invention is an electrochemical biosensor in which the reaction composition described above is screen printed onto working and counter electrodes.

In another aspect, the invention is a method for maintaining the activity of GDH-PQQ in a screen printed reagent composition.

DESCRIPTION OF THE PREFERRED EMBODIMENTS

Measuring the Glucose Content of Blood

The glucose contained in blood can be measured by various methods. Of particular interest are methods that are used by diabetic patients at home. These include optical and electrochemical methods, both of which may function by oxidizing glucose with an enzyme. The amount of glucose present is determined by measuring the color developed by an indicator or the electrical current produced by oxidation of a redox mediator when a potential is applied across a pair of electrodes. The present invention relates to the later method of measuring the glucose content of whole blood, in particular to the electrochemical biosensors that employ glucose dehydrogenase (GDH) and the co-factor pyrrolo-quinoline quinone (PQQ). The GDH-PQQ is combined with other components, including mediators, polymers, surfactants, buffers and thickeners, to produce a composition that is deposited on a pair of electrodes. When a potential is applied across the electrodes, the reaction of the GDH-PQQ with glucose and the redox reactions of the mediator produce an electrical current proportional to the amount of glucose in the blood sample that is in contact with the reactive composition.

Figure 1A:
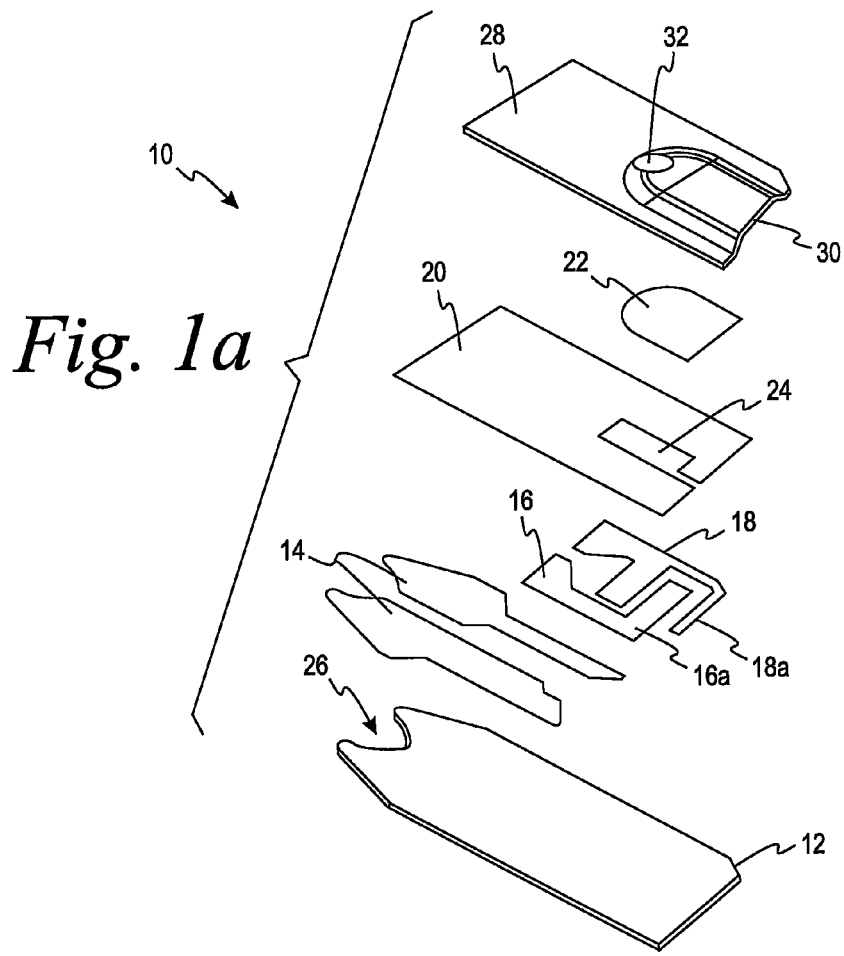
FIGS. 1a and b is an exploded view of a typical electrochemical sensor.
Figure 1B:
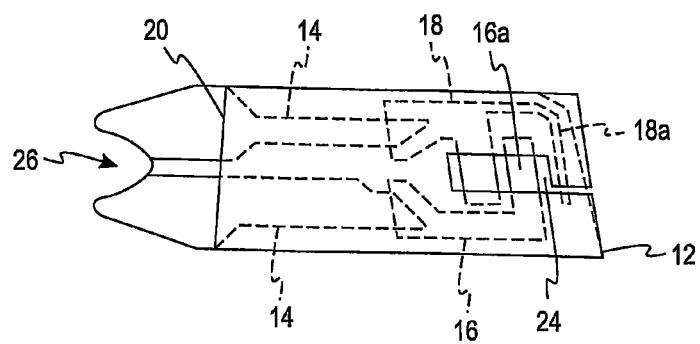

The present invention is not limited to a particular biosensor design among the many that have been disclosed in the art. An example of biosensors which may be used is described in U.S. Pat. No. 6,531,040, which is illustrated in FIG. 1a-b.

The biosensor 10 is shown in an exploded view in FIG. 1. It comprises an insulating base 12 upon which is printed in sequence (typically by screen printing techniques), an electrical conductor pattern 14, an electrode pattern (portions 16 and 18), an insulating (dielectric) pattern 20, and a reaction layer 22. The biosensor is completed by adding a cover layer 28. The capillary 30 formed between the cover layer 28 and the reagent layer 22, provides a flow path for the fluid test sample.

The reagents in reaction layer 22 react with the analytes in the fluid test sample (e.g., glucose in blood) and to produce an electrical current which is measured and correlated with the amount of the analyte present. The reaction layer 22 typically contains an enzyme or enzymes, and an electron acceptor. The enzyme reacts with the analyte to produce electrons, which are conveyed to the surface of the working electrode by an electron acceptor or mediator, which is reduced in response to the reaction between the analyte and the enzyme. In the present invention the enzyme is glucose dehydrogenase (GDH) and its co-factor pyrrolo-quinoline quinone (PQQ) and the mediator is a ferricyanide salt.

The two portions 16, 18 of the electrode pattern provide the respective working and counter electrodes necessary to electrochemically determine the analyte concentration. A feature of the design shown is that the working and counter electrodes are configured such that the major portion of the counter electrode is located downstream (in terms of the direction of fluid flow along the flow path) from the exposed portion of the working electrode 16a.

Counter electrode sub element 18a, however, is positioned up stream from working electrode upper element 16a so that when an amount of the test fluid sample (e.g., a whole blood sample) inadequate to completely cover the working electrode enters the capillary space, an electrical connection forms between counter electrode sub element 18a and exposed portion of the working electrode 16a due to the conductivity of the whole blood sample. The area of the counter electrode, however, that is available for contact by the whole blood sample is so small that only a very weak current can pass between the electrodes and, thus, through the current detector. By programming the current detector to give an error signal when the received signal is below a certain predetermined level, the sensor device informs the user that insufficient blood has entered the sensor's cavity and that another test should be conducted, or that more blood should be added. While the particular dimensions of the electrodes are not critical, the area of the counter electrode sub-element 18a is typically less than about 10% than that of the working electrode and, more specifically, less than about 6%. This element should be made as small as possible.

It was also contemplated in U.S. Pat. No. 6,531,040 that the reaction layer 22 could be removed from contact with counter electrode sub-element 18a, by producing a screen that does not print reagent ink over the counter electrode sub element 18a. This would starve the sub-element for reagent, thereby not allowing it to function as a proper counter electrode, so that an error condition is achieved when the test fluid sample fails to contact the bulk of the counter electrode 18. While sub element 18a is shown as being physically connected to, and therefore part of, the counter electrode 18, 18a may be physically disconnected from the rest of the counter electrode provided that it has its own connector and the sensor is equipped with a third contact to the detector.

The working and counter electrodes are generally printed using electrode ink, which is generally about 14 µm (0.00055") thick and typically contains electrochemically active carbon. Components of the conductor ink may be a mixture of carbon and silver that is chosen to provide a low chemical resistance path between the electrodes and the meter to which they are connected via contact with the conductive pattern at a fish tail end 26 of the sensor. The counter electrode may be comprised of silver/silver chloride, although carbon is preferred. To enhance the reproducibility of the meter reading, the dielectric pattern insulates the electrodes from the fluid test sample except in a defined area near the center of the electrode pattern 24. A defined area is important in this type of electrochemical determination because the measured current depends not only on the analyte concentration and the area of the reaction layer 22, but also on the area of the working electrode 16a that is exposed to the analyte-containing test sample.

A typical dielectric layer 20 comprises a UV-cured acrylate modified monomer, oligomer or polymer, and is about 10 μm (0.0004") thick. The dielectric layer also may be moisture-curable or heat-curable. The lid or cover 28 is adapted to mate with the base to form a space to receive the fluid test sample in which the counter and working electrodes are situated. Lid 28 provides a concave space 30, and is typically formed by embossing a flat sheet of deformable material. The lid 28 is punctured to provide an air vent 32 and joined to the base 12 in a sealing operation. The lid and base can be sealed together by sonic welding in which the base 12 and lid 28 are first aligned and then pressed together between a vibratory heat sealing member or horn and a stationary jaw, with contact only with the flat, non-embossed regions of the lid. The embossed lid and base may also be joined by using an adhesive material on the underside of the lid. The method of joining the lid and base are more fully described in U.S. Pat. No. 5,798,031.

Suitable materials for the insulating base 12 include polycarbonate, polyethylene terephthalate, dimensionally stable vinyl and acrylic polymers, and polymer blends such as polycarbonate/polyethylene terephthalate, and metal foil structures (e.g., a nylon/aluminum/polyvinyl chloride laminate). The lid typically is fabricated from a deformable polymeric sheet material such as polycarbonate, or an embossable grade of polyethylene terephthalate, glycol modified polyethylene terephthalate, or a metal foil composition (e.g., an aluminum foil structure).

Other electrochemical sensors may be used in the present invention. Examples of an electrochemical sensor that can be used to measure glucose concentrations are those used in Bayer HealthCare's Ascensia™ AUTODISC® and Ascensia™ ELITE® systems. More details on such electrochemical sensors may be found in U.S. Pat. Nos. 5,120,420 and 5,320,732. Other electrochemical sensors are available from Matsushita Electric Industrial Company. A further example of an electrochemical sensor that may be used in an amperometric monitoring system is disclosed in U.S. Pat. No. 5,429,735.

The electrochemical sensors may be located in a blood glucose sensor dispensing instrument loaded with a plurality of sensors. One example of a sensor pack loaded in a sensor dispensing instrument is disclosed in U.S. Pat. No. 5,660,791.

When an electrochemical sensor is placed in a suitable measuring instrument and a blood sample is introduced, a potential is applied across the electrodes and the electrical current is measured, correlated with the glucose content of the sample, and reported to the user.

The amperometric sensors may apply a fixed potential across the electrodes and the current produced is measured over a predetermined period of time, which may be quite short, say 5 to 10 seconds, in order to correct for the bias that may be present due to premature reduction of the mediator. That period is referred to as "burn period". The current rises to a peak and then declines, while the sample is re-hydrating the reagent layer, enabling the oxidation and reduction reactions to occur. After this burn period, the applied potential is removed or at least reduced during a resting period that allows the reactions to occur. Then, the potential is reapplied and the current measured over a predetermined "read" period (e.g., ten seconds). Since reduced mediator is present as the result of the concomitant oxidation of the enzyme, the current produced initially is high, but then it declines asymptotically and approaches a steady state condition. The current recorded at the end of the short "read" period is used to determine the glucose content of the blood sample, through a previously obtained correlation between the current at the end of the read period and the glucose contained in test samples having known concentrations.

Reactive Composition

The composition that reacts with a sample of blood in an electrochemical biosensor must provide a consistent response from one sensor to the next. Consistent response is important to users that rely on the results to adjust their diet or medication. It follows that changes in activity of the reagents over the shelf life of the biosensor should be as small as possible, but at least predictable, so that adjustment of the results can be made. The present invention solves a problem discovered where the enzyme-co-factor GDH-PQQ was to be used in an electrochemical biosensor in which the reactive composition was to be screen printed onto the sensor's electrodes. The inventors found that GDH-PQQ in components commonly used in screen printing caused the GDH-PQQ to lose activity.

Figure 2:
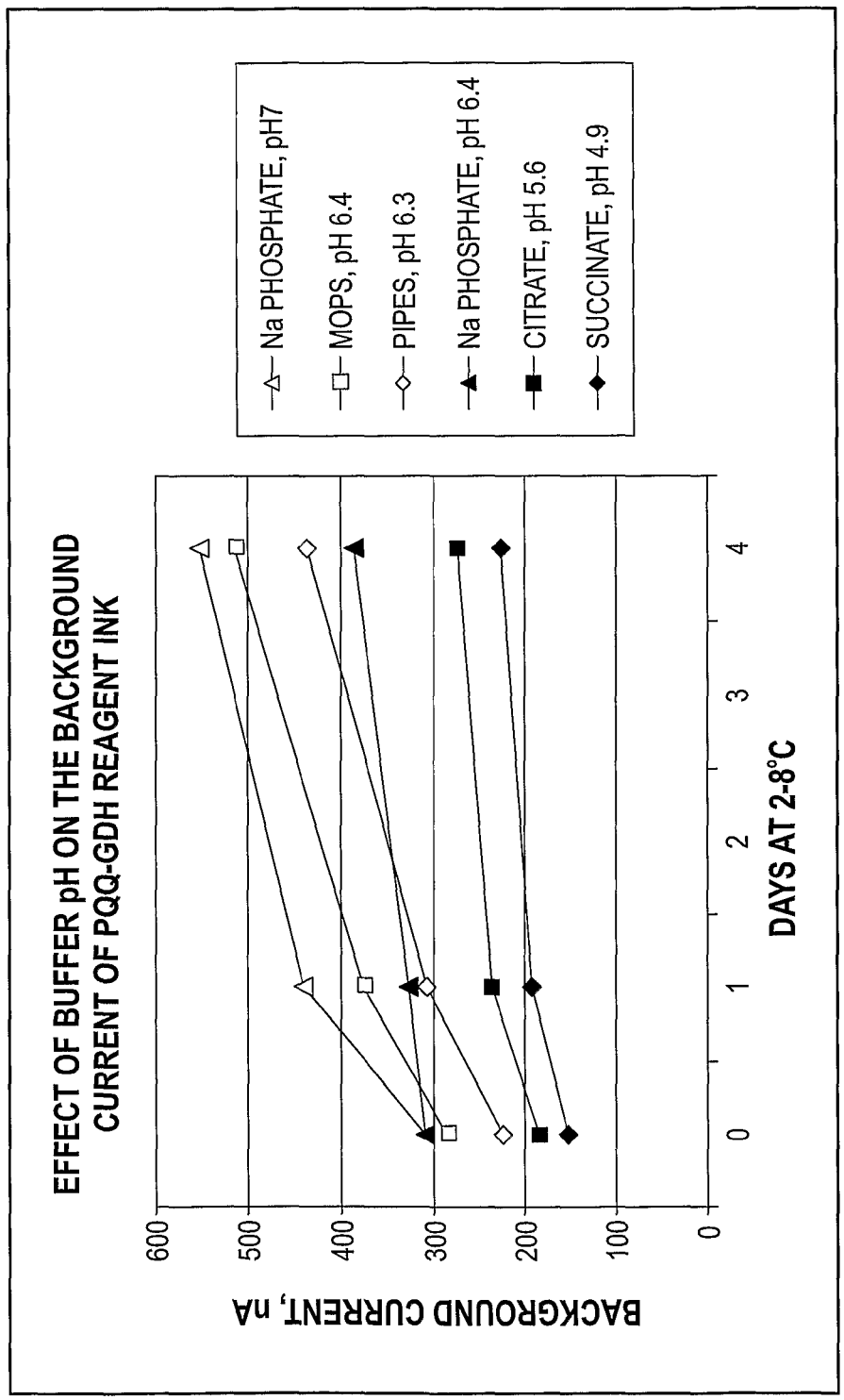
FIG. 2 is a plot of reagent background current versus different buffers.

Mixtures of GDH-PQQ with potassium ferricyanide as a redox mediator were prepared in a series of buffers. Although it was known that GDH-PQQ preferred a neutral pH, buffers, including acetate, citrate and succinate buffers, providing a pH in the range of from about 4.5 to about 6.5 and, more specifically, from about 5.0 to about 6.0 were found to be more desirable, since the mediator ferricyanide is more stable in acidic pH (see FIG. 2).

Figure 3:
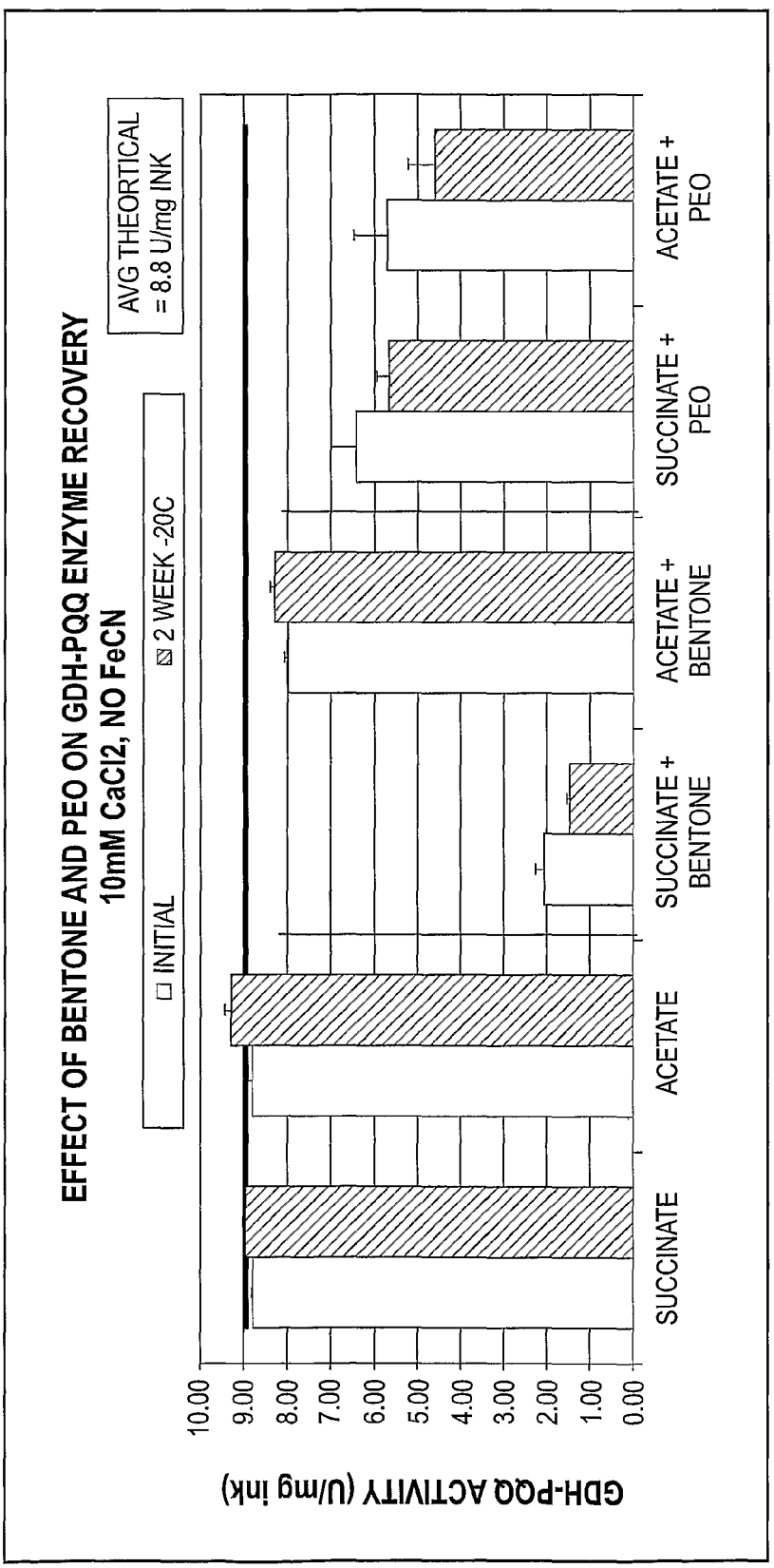
FIG. 3 is a bar chart showing the effect on enzyme activity of certain components in reagent formulations.

It was found that certain polymeric materials also appeared to cause loss of activity even when low pH buffers were used. Two polymers used to form a carrier for the enzyme and redox mediator were tested with 75 mM calcium acetate and 75 mM sodium succinate buffers. No potassium ferricyanide was included. The results are shown in FIG. 3 in which the initial effect on enzyme activity is shown and compared with the effect after two weeks at −20° C. It can be seen that when only succinate and acetate buffers were present in a solution that contains 8.8 units of GDH-PQQ per milligram of reagent ink and 10 mM $CaCl_2$, but without ferricyanide, the buffers did not cause significant loss of activity after two weeks at −20° C. The enzyme activity was determined with a Beckman SYNCHRON CX 4® Delta instrument measuring the rate of diformazan formation at 560 nm formed by the reduction of nitrotetrazolium blue (NBT) with phenazine methosulfate (PMS) at 37° C. However, when additives previously used to prepare screen printing inks are included, significant losses of activity were seen. Bentone, a clay thickener, supplied by RHEOX, Inc. was included at 1.3 wt % in the buffer solution. The results shown in FIG. 3 indicate that in the acetate buffer, bentone caused an enzyme activity loss of about 10%, while in the succinate buffer, about 90% of the enzyme activity was lost from fresh reagent and also from reagent stored at −20° C. for two weeks. Activity was lost also when 7.4 wt % polyethylene oxide was added to the buffer solutions, although the difference in the effect of the buffers is notable. It can be concluded that reagent formulations containing GDH-PQQ in combination with bentone or polyethylene oxide showed lower enzyme activities and are therefore less desirable thickening components of a screen printable reagent ink.

Figure 4:
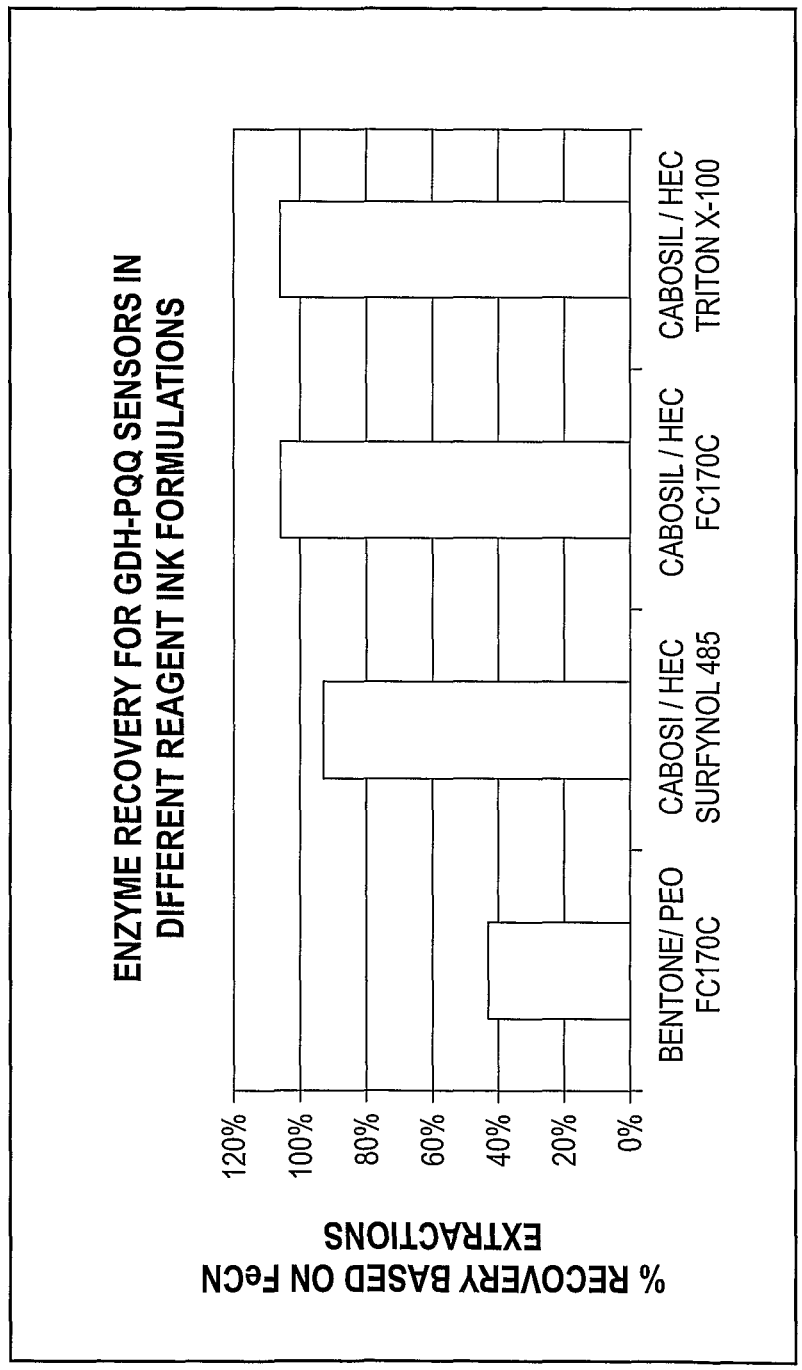
FIG. 4 is a bar chart showing the effect on enzyme activity of reagent formulations of the invention.

Investigation of the effect of other thickeners that were potentially suitable replacements for bentone and polyethylene oxide resulted in the discovery that certain materials produced reagent ink suitable for screen printing without causing loss of activity of GDH-PQQ. Improved results are illustrated in FIG. 4. In the tests reported in FIG. 4, 4 to 8 u/mg of GDH-PQQ, 1.6 wt % of CAB-O-SIL M5® un-treated fumed silica, 4.5 to 6.5 wt % hydroxyethyl cellulose (HEC), and several surfactants were added to acetate buffer solution. The activity of the enzyme was measured with the PMS/NBT enzyme assay on the Beckman analyzer at 37° C. CAB-O-SIL M5® was suitable in combination with HEC. It is clear that the combination of CAB-O-SIL M5® and HEC did not cause a loss of enzyme activity during the period tested.

As has been shown, hydroxyethyl cellulose can be used as a matrix component in the reactant layer in electrochemical biosensors using GDH-PQQ without causing undue loss of enzyme activity. Other related hydrophilic polymers may also be used, to make the viscosity of the composition suitable for screen printing. Other cellulose derivatives include, but are not limited to, sodium carboxymethyl cellulose, hydroxypropylcellulose, hydroxyethylcellulose, or hydroxypropyl methylcellulose. Other water soluble polymers that may be useful include xanthan gums, guar gum, locust bean gum, carrageenan, agarose, and synthetic polymers including polyvinyl alcohol, polyvinyl pyrrolidone, and the like.

CAB-O-SIL M5® is an amorphous untreated fumed silica that has been shown to provide the needed physical properties to inks used in screen printing of reagent layers of the invention. This untreated hydrophilic silica is to be distinguished from the treated silica taught in several earlier patents to balance hydrophobic and hydrophilic properties. Alternative water-insoluble thickening agents include, but are not limited to, talc, mica, diatomaceous earth, natural and modified clays, for example bentonite clays, hectorite clays (e.g., OPTIGEL sH™ from IMV Nevada), sepiolites (e.g., SEPIOGEL F™ from IMV Nevada), montmorilonites (e.g., IGB™ clay from IMV Nevada), Saponites (e.g., SEPIOGEL F™ and IMVITE 1016™ from IMV Nevada and LAPONITE™ from Southern clay products), and the like.

As shown in FIG. 4, the selection of the surfactants may also affect the activity of GDH-PQQ. TRITON X-100™, an alkyl aryl polyether alcohol, supplied by Sigma is very suitable. However, others including FC 170C™, a product of 3M, SURFYNOL 485™, a product of Air Products and Chemicals, Inc., and PLURONIC L62 D™, a product of BASF are considered to be useful in formulations of the invention.

Preferred reagent compositions for screen-printing biosensor according to the invention contain:
- about 30 to about 200 mM and, more specifically, about 50 to about 150 mM of a buffer, preferably calcium acetate
- about 5 to about 50 mM of $CaCl_2$
- up to about 0.5 wt % of a surfactant, based on the total weight of the composition
- about 2 to about 10 wt % of a cellulose derivative, preferably hydroxyethyl cellulose, based on the total weight of the composition
- about 1 to about 6 wt % of amorphous untreated silica, based on the total weight of the composition
- about 10 to about 20 wt % potassium ferricyanide as a mediator, based on the total weight of the composition
- about 1 to about 8 units of GDH-PQQ enzyme-cofactor for each milligram of the total weight of the composition
- a viscosity of from about 60,000 to about 180,000 cps (mPa·s).

Example 1

A 75 mM calcium acetate buffer having a pH of 5.3 was prepared by adding calcium acetate and glacial acetic acid. To the buffer solution, the following compounds were added: 10 mM $CaCl_2$, 0.05 wt % TRITON X-100™ surfactant, 1-3 wt % CABOSIL M5™ amorphous untreated fumed silica powder, and 4-8 wt % hydroxyethyl celluose. After allowing 16 hours for hydration of the silica and cellulose, 15-20 wt % potassium ferricyanide and, 3 to 8 units of GDH-PQQ were added to each milligram of reagent ink. The reagent ink was mixed at 600 rpm with a blade mixer for about 10 to 20 minutes to produce a reagent composition having a viscosity about 80,000 to 140,000 cps.

The reagent composition was screen printed onto a substrate containing electrodes and dried at 45-50° C. for 5 minutes.

Example 2

Figure 5:
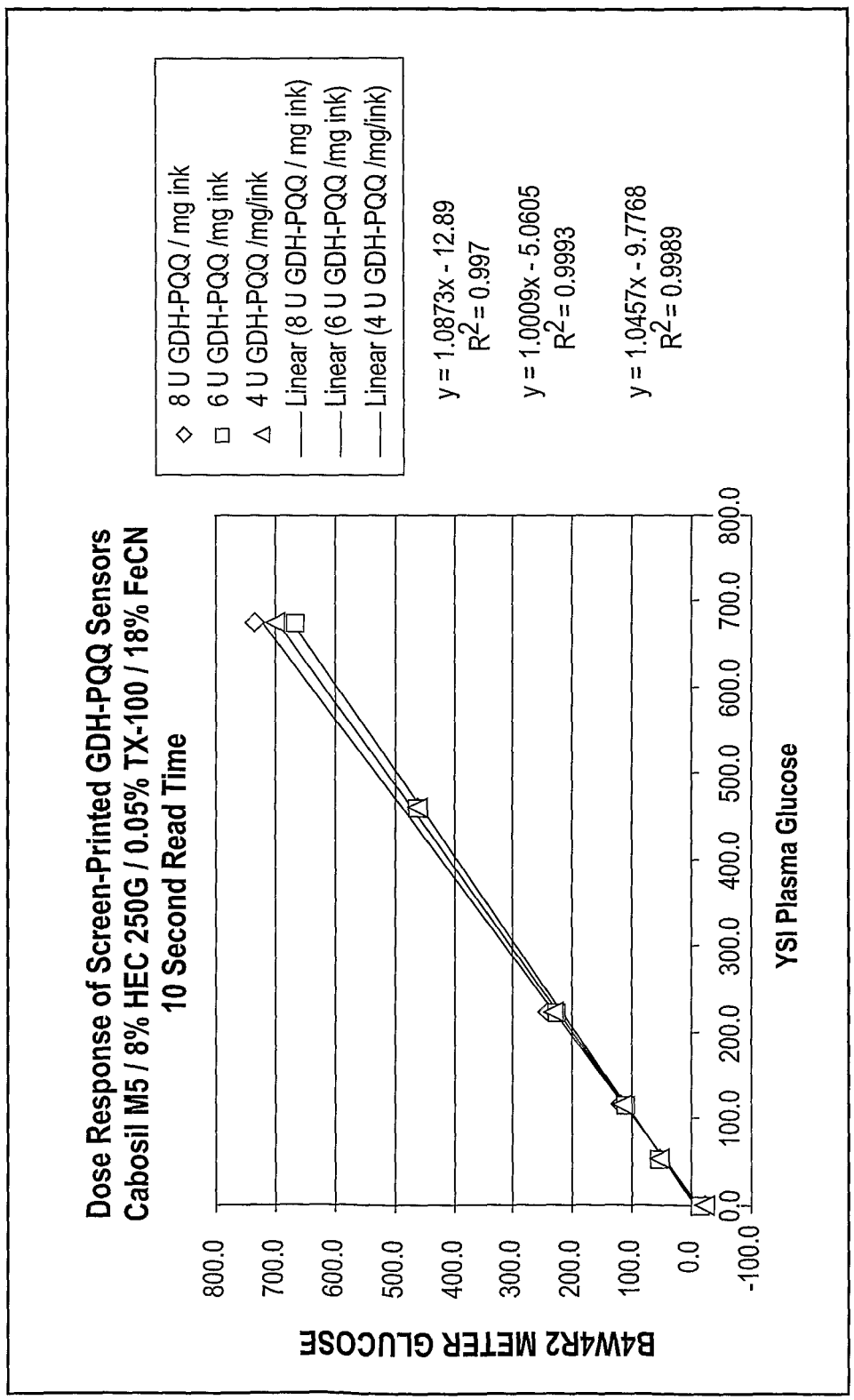
FIG. 5 is a plot of measured glucose versus a standard method.

Glucose sensors were prepared using the reagent composition of Example 1 and tested with blood samples containing known glucose contents and having 40% hematocrit. A potential of 200 to 400 millivolts was applied to the electrodes and the current measured ten seconds after applying the potential was used to determine the glucose contents of the samples. The results of these tests are shown in FIG. 5 where the response of an Ascensia™ AUTODISC® Glucose meter programmed for a 10 second test time are plotted against the glucose content measured by the industry standard YSI glucose instrument. It can be seen that a linear response was obtained, that was relatively insensitive to the concentration of the enzyme-cofactor concentration within the range studied.

Figure 6:
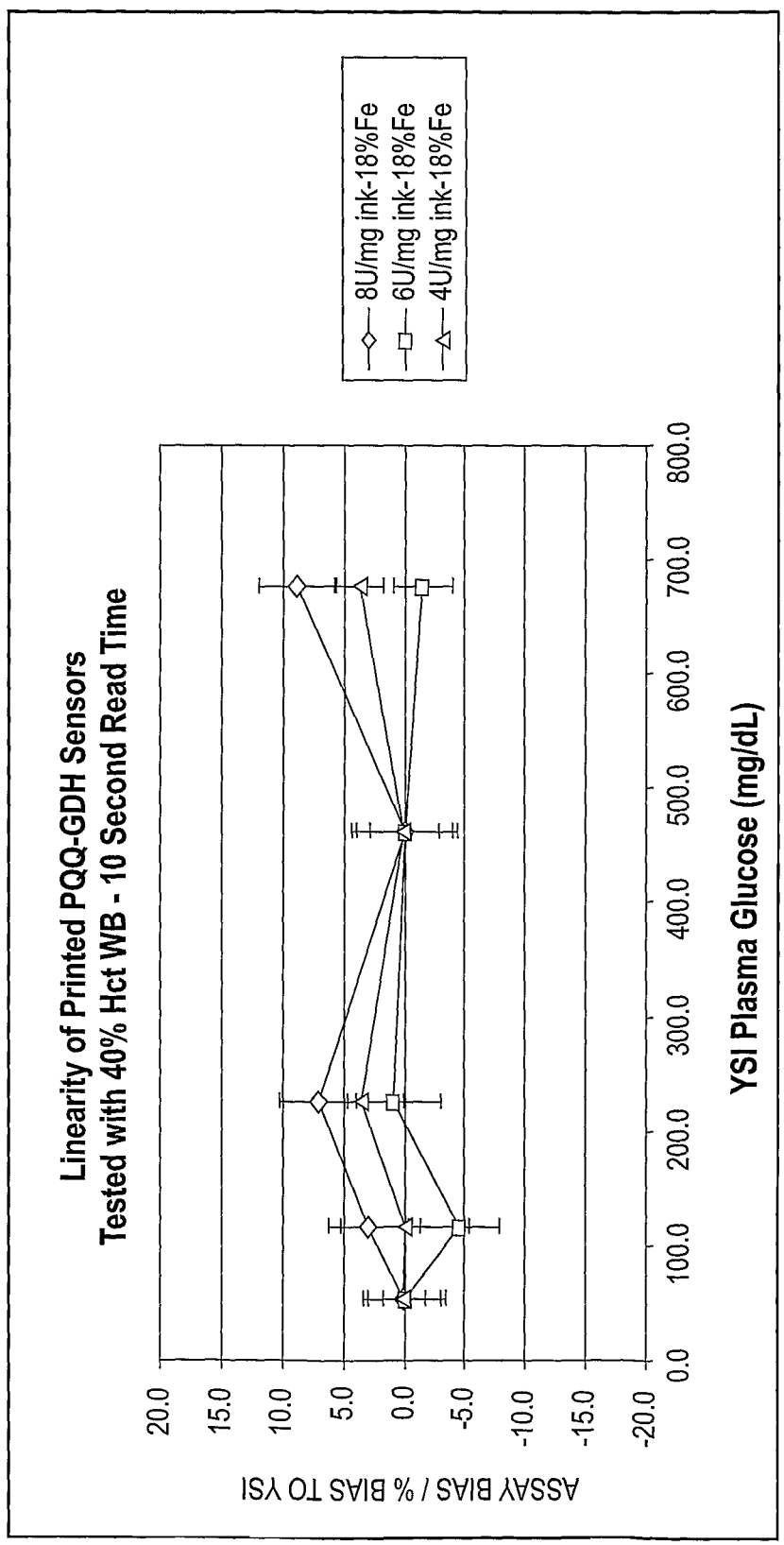
FIG. 6 is a plot of the deviation in measurements of FIG. 5.

The sensors also demonstrated good dose response when compared with the results obtained from the YSI instrument, an industry standard. The bias relative to the YSI instrument results is shown in FIG. 6. The bias was within ±5% for samples with ≤400 mg/dL glucose and within ±10% for samples with 680 mg/dL glucose.

Alternative Embodiment A

A reagent composition for screen-printing electrochemical biosensors comprising:
(a) glucose dehydrogenase (GDH) and co-factor pyrroloquinoline quinone (PQQ) for oxidizing glucose in a biological sample;
(b) a hydrophilic polymer selected from the group consisting of cellulose derivatives, natural gums and gels, and water soluble synthetic polymers;
(c) a thickening agent selected from the group consisting of amorphous untreated silica powder, talc, mica, diatomaceous earth, and natural and modified clays;
(d) a buffer sufficient to maintain pH in the range of from about 4.5 to about 6.5 to 6.0;
(e) a surfactant; and
(f) a mediator.

Alternative Embodiment B

The reagent composition of Alternative Embodiment A wherein said buffer is an acetate, citrate, or succinate buffer.

Alternative Embodiment C

The reagent composition of Alternative Embodiment A wherein said surfactant is an alkyl aryl polyether alcohol.

Alternative Embodiment D

The reagent composition of Alternative Embodiment A wherein said mediator is potassium ferricyanide.

Alternative Embodiment E

The reagent composition of Alternative Embodiment A wherein the buffer is from 5.0 to 6.0.

Alternative Embodiment F

The reagent composition of Alternative Embodiment E wherein said composition has a viscosity of about 60,000 to about 180,000 cps (mPa·s).

Alternative Embodiment G

The reagent composition of Alternative Embodiment A wherein said hydrophilic polymer is a cellulose derivative selected from the group consisting of sodium carboxymethyl cellulose, hydroxy ethyl cellulose, hydroxy propyl cellulose, and hydroxy propylmethyl cellulose.

Alternative Embodiment H

The reagent composition of Alternative Embodiment G wherein said hydrophilic polymer is hydroxyethyl cellulose.

Alternative Embodiment I

The reagent composition of Alternative Embodiment A wherein said thickening agent is amorphous untreated silica powder.

Alternative Embodiment J

The reagent composition of Alternative Embodiment I wherein said amorphous untreated silica powder is hydrophilic.

Alternative Embodiment K

The reagent composition of Alternative Embodiment A wherein 1-8 units of said GDH-PQQ is present for each milligram of the total weight of the composition.

Alternative Embodiment L

The reagent composition of Alternative Embodiment B wherein said buffer is present in about 30 to about 200 mM.

Alternative Embodiment M

The reagent composition of Alternative Embodiment C wherein up to about 0.5 wt % of said polyether alcohol is present, based on the total weight of the composition.

Alternative Embodiment N

The reagent composition of Alternative Embodiment D wherein about 10 to about 20 wt % of said potassium ferricyanide, based on the total weight of the composition.

Alternative Embodiment O

The reagent composition of Alternative Embodiment G wherein about 2 to about 10 wt % of said cellulose derivative is present, based on the total weight of the composition.

Alternative Embodiment P

The reagent composition of Alternative Embodiment I wherein about 1 to about 6 wt % of said amorphous untreated silica powder is present, based on the total weight of the composition.

Alternative Embodiment Q

The reagent composition of Alternative Embodiment A further comprising about 5 to about 50 mM of calcium chloride.

Alternative Embodiment R

An electrochemical biosensor comprising:
(a) a non-porous substrate;
(b) working and counter electrodes disposed on said substrate;
(c) a reagent composition screen-printed on said electrodes, said composition comprising:
 (1) about 1-8 units of glucose dehydrogenase (GDH) and co-factor pyrrolo-quinoline quinone (PQQ) for oxidizing glucose in a biological sample, for each milligram of the total weight of said composition;
 (2) a hydrophilic polymer selected from the group consisting of cellulose derivatives, natural gums and gels, and water soluble synthetic polymers;
 (3) a thickening agent selected from the group consisting of amorphous untreated silica powder, talc, mica, diatomaceous earth, and natural and modified clays;
 (4) a buffer sufficient to maintain pH in the range of from about 4.5 to about 6.5,
 (5) a surfactant, and
 (6) a mediator; and
(d) a protective cover for said electrodes and said reagent composition.

Alternative Embodiment S

The electrochemical biosensor of Alternative Embodiment R wherein said buffer is about 30 to about 200 mM of an acetate, citrate, or succinate buffer.

Alternative Embodiment T

The electrochemical biosensor of Alternative Embodiment R wherein said surfactant is up to about 0.5 wt. % of an alkyl aryl polyether alcohol, based on the total weight of said composition.

Alternative Embodiment U

The electrochemical biosensor of Alternative Embodiment R wherein said mediator is about 10 to about 20 wt % of potassium ferricyanide, based on the total weight of said composition.

Alternative Embodiment V

The electrochemical biosensor of Alternative Embodiment R wherein sufficient amounts of components (c)(2) and (c)(3) are included to provide a composition suitable for use in screen printing.

Alternative Embodiment W

The electrochemical biosensor of Alternative Embodiment R wherein said composition has a viscosity of about 60,000 to about 180,000 cps (mPa·s).

Alternative Embodiment X

The electrochemical biosensor of Alternative Embodiment R wherein said hydrophilic polymer is about 2 to about 10 wt % of a cellulose derivative selected from the group consisting of sodium carboxy methyl cellulose, hydroxy ethyl cellulose, hydroxy propyl cellulose, and hydroxy propyl methyl cellulose, based on the total weight of said composition.

Alternative Embodiment Y

The electrochemical biosensor of Alternative Embodiment X wherein said hydrophilic polymer is hydroxy ethyl cellulose.

Alternative Embodiment Z

The electrochemical biosensor of Alternative Embodiment R wherein said thickening agent is from about 1 to about 6 wt % of an amorphous untreated silica powder, based on the total weight of said composition.

Alternative Embodiment AA

The electrochemical biosensor of Alternative Embodiment Z wherein said amorphous untreated silica powder is hydrophilic.

Alternative Embodiment BB

The electrochemical biosensor of Alternative Embodiment R wherein said reagent composition includes from about 5 to about 50 mM of calcium chloride.

Alternative Process CC

A method of maintaining activity of glucose dehydrogenase (GDH) and co-factor pyrrolo-quinoline quinone (PQQ) in a screen-printed reagent composition used in an electrochemical biosensor comprising screen printing a reagent composition, the method comprising the acts of:
(a) glucose dehydrogenase (GDH) and co-factor pyrrolo-quinoline quinone (PQQ) for oxidizing glucose in a biological sample;
(b) a hydrophilic polymer selected from the group consisting of cellulose derivatives, natural gums and gels, and water soluble synthetic polymers;
(c) a thickening agent selected from the group consisting of amorphous untreated silica powder, talc, mica, diatomaceous earth, and natural and modified clays;
(d) a buffer sufficient to maintain pH in the range of from about 4.5 to about 6.5;
(e) a surfactant; and
(f) a mediator.

Alternative Process DD

The method of Alternative Process CC wherein said hydrophilic polymer is a cellulose derivative selected from the group consisting of sodium carboxy methyl cellulose, hydroxy ethyl cellulose, hydroxy propyl cellulose, and hydroxy propyl methyl cellulose.

Alternative Process EE

The method of Alternative Process CC wherein said thickening agent is amorphous untreated silica powder.

Alternative Process FF

The method of Alternative Process CC wherein said the pH is maintained in the range of from 5.0 to 6.0.

While the invention is susceptible to various modifications and alternative forms, specific embodiments are shown by way of example in the drawings and described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

The invention claimed is:

1. A reagent composition for making electrochemical biosensors comprising:
   (a) glucose dehydrogenase (GDH) and co-factor pyrrolo-quinoline quinone (PQQ) for oxidizing glucose in a biological sample;
   (b) 2 to about 10 wt % of a hydrophilic polymer selected from cellulose derivatives, based on the total weight of the composition;
   (c) about 1 to about 6 wt % of amorphous untreated silica powder, based on the total weight of the composition;
   (d) a buffer sufficient to maintain pH in the range of from about 4.5 to about 6.5;
   (e) a surfactant; and
   (f) a mediator.

2. The reagent composition of claim 1, wherein said buffer is an acetate, citrate, or succinate buffer.

3. The reagent composition of claim 2, wherein said buffer is present in about 30 to about 200 mM.

4. The reagent composition of claim 3, wherein said buffer is present in about 50 to about 150 mM.

5. The reagent composition of claim 1, wherein said surfactant is an alkyl aryl polyether alcohol.

6. The reagent composition of claim 5, wherein up to about 0.5 wt % of said polyether alcohol is present, based on the total weight of the composition.

7. The reagent composition of claim 1, wherein said mediator is potassium ferricyanide.

8. The reagent composition of claim 7, wherein about 10 to about 20 wt % of said potassium ferricyanide is present, based on the total weight of the composition.

9. The reagent composition of claim 1, wherein the pH of the buffer ranges from 5.0 to 6.0.

10. The reagent composition of claim 9, wherein said composition has a viscosity of about 60,000 to about 180,000 cps (mPa·s).

11. The reagent composition of claim 1, wherein said hydrophilic polymer is a cellulose derivative selected from the group consisting of sodium carboxymethyl cellulose, hydroxy ethyl cellulose, hydroxy propyl cellulose, and hydroxy propylmethyl cellulose.

12. The reagent composition of claim 11, wherein said hydrophilic polymer is hydroxyethyl cellulose.

13. The reagent composition of claim 1, wherein 1-8 units of said GDH-PQQ is present for each milligram of the total weight of the composition.

14. The reagent composition of claim 1, wherein said amorphous untreated silica powder is hydrophilic.

15. The reagent composition of claim 1, further comprising about 5 to about 50 mM of calcium chloride.

16. The reagent composition of claim 1, wherein the bias associated therewith is within ±10%.

17. The reagent composition of claim 1, wherein the bias associated therewith is within ±5% for samples having ≤400 mg/dL glucose.

18. A reagent composition for making electrochemical biosensors comprising:
- (a) glucose dehydrogenase (GDH) and co-factor pyrroloquinoline quinone (PQQ) for oxidizing glucose in a biological sample, wherein about 1-8 units of said GDH-PQQ is present for each milligram of the total weight of the composition;
- (b) 2 to about 10 wt % of a hydrophilic polymer selected from cellulose derivatives, based on the total weight of the composition;
- (c) about 1 to about 6 wt % of a thickening agent selected from the group consisting of amorphous untreated silica powder, talc, mica, diatomaceous earth, and natural and modified clays, based on the total weight of the composition;
- (d) about 30 to about 200 mM of a buffer sufficient to maintain pH in the range of from about 4.5 to about 6.5;
- (e) up to about 0.5 wt % of a surfactant, based on the total weight of the composition; and
- (f) about 10 to about 20 wt % of a mediator, based on the total weight of the composition.

19. The reagent composition of claim 18, further comprising about 5 to about 50 mM of calcium chloride.

20. The reagent composition of claim 18, wherein the bias associated therewith is within ±10%.

21. The reagent composition of claim 18, wherein the bias associated therewith is within ±5% for samples having ≤400 mg/dL glucose.

22. A reagent composition for making electrochemical biosensors comprising:
- (a) glucose dehydrogenase (GDH) and co-factor pyrroloquinoline quinone (PQQ) for oxidizing glucose in a biological sample;
- (b) 2 to about 10 wt % of a hydroxyethyl cellulose polymer;
- (c) amorphous untreated silica powder;
- (d) a calcium acetate buffer sufficient to maintain pH in the range of from about 4.5 to about 6.5;
- (e) an alkyl aryl polyether alcohol surfactant; and
- (f) a potassium ferricyanide mediator.

23. The reagent composition of claim 22, further comprising calcium chloride.

24. The reagent composition of claim 22, wherein the bias associated therewith is within ±10%.

25. The reagent composition of claim 22, wherein the bias associated therewith is within ±5% for samples having ≤400 mg/dL glucose.

26. A reagent composition for making electrochemical biosensors comprising:
- (a) an enzyme for oxidizing glucose in a biological sample;
- (b) 2 to about 10 wt % of a hydrophilic polymer selected from cellulose derivatives, based on the total weight of the composition;
- (c) about 1 to about 6 wt % of a thickening agent selected from the group consisting of amorphous untreated silica powder, talc, mica, diatomaceous earth, and natural and modified clays, based on the total weight of the composition;
- (d) a buffer sufficient to maintain pH in the range of from about 4.5 to about 6.5;
- (e) a surfactant; and
- (f) a mediator.

27. The reagent composition of claim 26, wherein the bias associated therewith is within ±10%.

28. The reagent composition of claim 26, wherein the bias associated therewith is within ±5% for samples having ≤400 mg/dL glucose.

* * * * *